US007790692B2

(12) United States Patent
Kubo et al.

(10) Patent No.: US 7,790,692 B2
(45) Date of Patent: Sep. 7, 2010

(54) HEPATOCYTE GROWTH FACTOR NUCLEIC ACID SEQUENCE TO ENHANCE MUSCULOCUTANEOUS FLAP SURVIVAL

(75) Inventors: Tateki Kubo, Osaka (JP); Marvin A. Tanag, Osaka (JP); Kenji Yano, Osaka (JP); Ko Hosokawa, Osaka (JP); Ryuichi Morishita, Osaka (JP)

(73) Assignee: Anges MG Inc., Osaka (JP)

( * ) Notice: Subject to any disclaimer, the term of this patent is extended or adjusted under 35 U.S.C. 154(b) by 520 days.

(21) Appl. No.: 11/094,484

(22) Filed: Mar. 31, 2005

(65) Prior Publication Data

US 2005/0261231 A1 Nov. 24, 2005

Related U.S. Application Data

(60) Provisional application No. 60/557,835, filed on Mar. 31, 2004.

(51) Int. Cl.
*A61K 48/00* (2006.01)
*C07K 14/475* (2006.01)
(52) U.S. Cl. ......................................... 514/44; 530/399
(58) Field of Classification Search ....................... None
See application file for complete search history.

(56) References Cited

FOREIGN PATENT DOCUMENTS

WO    WO 02/083185 A1    10/2002

OTHER PUBLICATIONS

Orkin and Motulsky, "Report and Recommendations of the Panel to Assess the NIH Investment in Research on Gene Therapy", NIH home page (Dec. 7, 1995).*
Rudinger, In "Peptide Hormones" (ed. J.A.Parsons) University Park Press, Baltimore, pp. 1-7 (1976).*
Takebe et al, Molecular and Cellular Biology (1988) 8: 466-472.*
Ely et al., "7-Transverse Rectus Abdominis Musculocutaneous Flap (TRAM Flap)—Experimental Model in Rats," 2003, pp. 46-53.
Tashiro et al., "Deduced Primary Structure of Rat Hepatocyte Growth Factor and Expression of the mRNA in Rat Tissues," Proc. Natl. Acad. Sci., Cell Biology, vol. 87, 1990, pp. 3200-3204.
Wong et al., "Visualization of Subsurface Blood Vessels by Color Doppler Optical Coherence Tomography in Rats: Before and After Hemostatic therapy," Gastrointestinal Endoscopy, vol. 55, No. 1, 2002, pp. 88-95.
Bevan et al., "Diverse and Potent Activities of HGF/SF in Skin Wound Repair," Journal of Pathology, vol. 203, Pathological Society of Great Britain and Ireland, 2004, pp. 831-838.
Hamoen et al., "Transient Hyperproliferation of a Transgenic Human Epidermis Expressing Hepatocyte Growth Factor," Cell Transplantation, vol. 11, 2002, pp. 385-395.
Kondo et al., "Treatment of Acute Myocardinal Infraction by Hepatocyte Growth Factor Gene Transfer," Journal of the American College of Cardiology, vol. 44, No. 3, The American College of Cardiology Foundation, 2004, pp. 644.653.
Matsumoto et al., "HGF in Regenerative Medicine: Roles in Regeneration System and Potential Therapeutic Application," Biotherapy, vol. 15, No. 2, 2001, pp. 95-104.
Nakanishi et al., "Gene Transfer of Human Hepatocyte Growth Factor into Rat Skin Wounds Mediated by Liposomes Coated with The Sendai Virus (Hemagglutinating Virus of Japan," American Journal of Pathology, vol. 161, No. 5, American Society for Investigative Pathology, 2002, pp. 1761-1772.
Xue et al., "Attenuated Acute Liver Injury in Mice by Naked Hepatocyte Growth Factor Gene Transfer into Skeletal Muscle with Electroporation," Downloaded from gut.bmjjournals.com, Aug. 1, 2005, pp. 558-562, www.gutjnl.com.
Yamaguchi et al., "Cutaneous Wound Healing: An Update," The Journal of Dermatology, vol. 28, 2001, pp. 521-534.
Yamaura et al., "Suppression of Acute and Chronic Rejection by Hepatocyte Growth Factor in a Murine Model of Cardiac Transplantation," American Hear Association, Inc., Circulation is Available at http://www.curculationaha.org, pp. 1650-1657.
Harms et al.; Comparison of bovine leukemia virus (BLV) and CMV promoter-driven reporter gene expression in BLV-infected and non-infected cells; *Genetic Vaccines and Therapy*; 2004, 2:11, pp. 1-9.
Cheng et al; "A rapid and efficient method to express target genes in mammalian cells by baculovirus"; *World J. Gastroenterol*; 2004; 10(11):1612-1618.
Nakagawa et al.; "Improvement of survival of skin flaps by combined gene transfer of hepatocyte growth factor and prostacyclin synthase"; *The Journal of Gene Medicine*; 2007; 9:1087-1094.

* cited by examiner

*Primary Examiner*—Robert C Hayes
(74) *Attorney, Agent, or Firm*—Foley & Lardner LLP

(57) ABSTRACT

The present invention relates to the use of growth factors in improving tissue survival. In particular, the invention describes methods for enhancing organ transplant, musculocutaneous flap or skin graft survival by administering a nucleic acid sequence encoding hepatocyte growth factor.

12 Claims, 3 Drawing Sheets

SEQUENCE LISTING

<160> NUMBER OF SEQ ID NOS: 3

<210> SEQ ID NO 1
<211> LENGTH: 2187
<212> TYPE: DNA
<213> ORGANISM: Homo sapiens

<400> SEQUENCE: 1

| | | | | | | |
|---|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgttttttgat | aaagcaagaa | aacaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | agagtggcat | caaatgtcag | ccctggagtt | ccatgatacc | acacgaacac | 480 |
| agcttttttgc | cttcgagcta | tcggggtaaa | gacctacagg | aaaactactg | tcgaaatcct | 540 |
| cgagggggaag | aagggggacc | ctggtgtttc | acaagcaatc | cagaggtacg | ctacgaagtc | 600 |
| tgtgacattc | ctcagtgttc | agaagttgaa | tgcatgacct | gcaatgggga | gagttatcga | 660 |
| ggtctcatgg | atcatacaga | atcaggcaag | atttgtcagc | gctgggatca | tcagacacca | 720 |
| caccggcaca | aattcttgcc | tgaaagatat | cccgacaagg | gctttgatga | taattattgc | 780 |
| cgcaatcccg | atggccagcc | gaggccatgg | tgctatactc | ttgaccctca | cacccgctgg | 840 |
| gagtactgtg | caattaaaac | atgcgctgac | aatactatga | atgacactga | tgttcctttg | 900 |
| gaaacaactg | aatgcatcca | aggtcaagga | gaaggctaca | ggggcactgt | caataccatt | 960 |
| tggaatggaa | ttccatgtca | gcgttgggat | tctcagtatc | ctcacgagca | tgacatgact | 1020 |
| cctgaaaatt | tcaagtgcaa | ggacctacga | gaaaattact | gccgaaatcc | agatgggtct | 1080 |
| gaatcaccct | ggtgttttac | cactgatcca | aacatccgag | ttggctactg | ctcccaaatt | 1140 |

-continued

```
ccaaactgtg atatgtcaca tggacaagat tgttatcgtg ggaatggcaa aaattatatg    1200
ggcaacttat cccaaacaag atctggacta acatgttcaa tgtgggacaa gaacatggaa    1260
gacttacatc gtcatatctt ctgggaacca gatgcaagta agctgaatga gaattactgc    1320
cgaaatccag atgatgatgc tcatggaccc tggtgctaca cgggaaatcc actcattcct    1380
tgggattatt gccctatttc tcgttgtgaa ggtgatacca cacctacaat agtcaattta    1440
gaccatcccg taatatcttg tgccaaaacg aaacaattgc gagttgtaaa tgggattcca    1500
acacgaacaa acataggatg gatggttagt ttgagataca gaaataaaca tatctgcgga    1560
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt tcccagctg gtatatggcc ctgaaggatc agatctggtt     1740
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
caacataaaa tgagaatggt tcttggtgtc attgttcctg gtcgtggatg tgccattcca    2100
aatcgtcctg gtattttttgt ccgagtagca tattatgcaa aatggataca caaaattatt    2160
ttaacatata aggtaccaca gtcatag                                         2187
```

<210> SEQ ID NO 2
<211> LENGTH: 7681
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 2

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgctctagaa ctagctggat cctgccagcc    960
```

```
cgtccagcag caccatgtgg gtgaccaaac tcctgccagc cctgctgctg cagcatgtcc    1020
tcctgcatct cctcctgctc cccatcgcca tccctatgc agagggacaa aggaaaagaa     1080
gaaatacaat tcatgaattc aaaaaatcag caaagactac cctaatcaaa atagatccag    1140
cactgaagat aaaaaccaaa aaagtgaata ctgcagacca atgtgctaat agatgtacta    1200
ggaataaagg acttccattc acttgcaagg cttttgtttt tgataaagca agaaaacaat    1260
gcctctggtt ccccttcaat agcatgtcaa gtggagtgaa aaagaatttt ggccatgaat    1320
ttgacctcta tgaaaacaaa gactacatta gaaactgcat cattggtaaa ggacgcagct    1380
acaagggaac agtatctatc actaagagtg gcatcaaatg tcagccctgg agttccatga    1440
taccacacga acacagcttt ttgccttcga gctatcgggg taaagaccta caggaaaact    1500
actgtcgaaa tcctcgaggg gaagaagggg gaccctggtg tttcacaagc aatccagagg    1560
tacgctacga agtctgtgac attcctcagt gttcagaagt tgaatgcatg acctgcaatg    1620
gggagagtta tcgaggtctc atggatcata cagaatcagg caagatttgt cagcgctggg    1680
atcatcagac accacaccgg cacaaattct tgcctgaaag atatcccgac aagggctttg    1740
atgataatta ttgccgcaat cccgatggcc agccgaggcc atggtgctat actcttgacc    1800
ctcacacccg ctgggagtac tgtgcaatta aaacatgcgc tgacaatact atgaatgaca    1860
ctgatgttcc tttggaaaca actgaatgca tccaaggtca aggagaaggc tacaggggca    1920
ctgtcaatac catttggaat ggaattccat gtcagcgttg ggattctcag tatcctcacg    1980
agcatgacat gactcctgaa aatttcaagt gcaaggacct acgagaaaat tactgccgaa    2040
atccagatgg gtctgaatca ccctggtgtt ttaccactga tccaaacatc cgagttggct    2100
actgctccca aattccaaac tgtgatatgt cacatggaca agattgttat cgtgggaatg    2160
gcaaaaatta tatgggcaac ttatcccaaa caagatctgg actaacatgt tcaatgtggg    2220
acaagaacat ggaagactta catcgtcata tcttctggga accagatgca agtaagctga    2280
atgagaatta ctgccgaaat ccagatgatg atgctcatgg accctggtgc tacacgggaa    2340
atccactcat tccttgggat tattgcccta tttctcgttg tgaaggtgat accacaccta    2400
caatagtcaa tttagaccat cccgtaatat cttgtgccaa aacgaaacaa ttgcgagttg    2460
taaatgggat tccaacacga acaaacatag gatggatggt tagtttgaga tacagaaata    2520
aacatatctg cggaggatca ttgataaagg agagttgggt tcttactgca cgacagtgtt    2580
tcccttctcg agacttgaaa gattatgaag cttggcttgg aattcatgat gtccacggaa    2640
gaggagatga gaaatgcaaa caggttctca atgtttttcca gctggtatat ggccctgaag    2700
gatcagatct ggttttaatg aagcttgcca ggcctgctgt cdtggatgat tttgttagta    2760
cgattgattt acctaattat ggatgcacaa ttcctgaaaa gaccagttgc agtgtttatg    2820 gctgggggcta cactggattg atcaactatg atggcctatt acgagtggca catctctata    2880
taatgggaaa tgagaaatgc agccagcatc atcgagggaa ggtgactctg aatgagtctg    2940
aaatatgtgc tgggggctgaa agattggat caggaccatg tgaggggat tatggtggcc     3000 cacttgtttg tgagcaacat aaaatgagaa tggttcttgg tgtcattgtt cctggtcgtg    3060
gatgtgccat tccaaatcgt cctggtattt tgtccgagt agcatattat gcaaaatgga    3120
tacacaaaat tattttaaca tataaggtac cacagtcata gctgttaacc cgggtcgaag    3180
cggccgccac tgtgctggat atctgcagaa ttccaccaca ctggactagt ggatccgagc    3240
tcggtaccaa gcttaagttt aaaccgctga tcagcctcga ctgtgccttc tagttgccag    3300
```

```
ccatctgttg tttgcccctc ccccgtgcct tccttgaccc tggaaggtgc cactcccact    3360
gtcctttcct aataaaatga ggaaattgca tcgcattgtc tgagtaggtg tcattctatt    3420 ctgggggtg gggtggggca ggacagcaag ggggaggatt gggaagacaa tagcaggcat     3480
gctggggatg cggtgggctc tatggcttct gaggcggaaa gaaccagctg gggctctagg    3540
gggtatcccc acgcgccctg tagcggcgca ttaagcgcgg cgggtgtggt ggttacgcgc    3600
agcgtgaccg ctacacttgc cagcgcccta gcgcccgctc ctttcgcttt cttcccttcc    3660
tttctcgcca cgttcgccgg ctttccccgt caagctctaa atcggggct cccttttaggg    3720 ttccgattta gtgctttacg gcacctcgac cccaaaaaac ttgattaggg tgatggttca    3780
cgtagtgggc catcgccctg atagacggtt tttcgccctt tgacgttgga gtccacgttc    3840
tttaatagtg gactcttgtt ccaaactgga caacactca accctatctc ggtctattct     3900
tttgatttat aagggatttt gccgatttcg gcctattggt taaaaaatga gctgatttaa    3960
caaaaattta acgcgaatta attcgtggaa atgtgtgtca gttagggtgt ggaaagtccc    4020
caggctcccc agcaggcaga agtatgcaaa gcatgcatct caattagtca gcaaccaggt    4080
gtggaaagtc cccaggctcc ccagcaggca gaagtatgca aagcatgcat ctcaattagt    4140
cagcaaccat agtcccgccc ctaactccgc ccatcccgcc cctaactccg cccagttccg    4200
cccattctcc gccccatggc tgactaattt ttttttattta gcagaggcc gaggccgcct     4260 ctgcctctga gctattccag aagtagtgag gaggcttttt tggaggccta ggcttttgca    4320
aaaagctccc gggagcttgt atatccattt tcggatctga tcaagagaca ggatgaggat    4380
cgtttcgcat gattgaacaa gatggattgc acgcaggttc tccggccgct tgggtggaga    4440
ggctattcgg ctatgactgg gcacaacaga caatcggctg ctctgatgcc gccgtgttcc    4500
ggctgtcagc gcaggggcgc ccggttcttt ttgtcaagac cgacctgtcc ggtgccctga    4560
atgaactgca ggacgaggca gcgcggctat cgtggctggc cacgacgggc gttccttgcg    4620
cagctgtgct cgacgttgtc actgaagcgg gaagggactg gctgctattg ggcgaagtgc    4680
cggggcagga tctcctgtca tctcaccttg ctcctgccga gaaagtatcc atcatggctg    4740
atgcaatgcg gcggctgcat acgcttgatc cggctacctg cccattcgac caccaagcga    4800
aacatcgcat cgagcgagca cgtactcgga tggaagccgg tcttgtcgat caggatgatc    4860
tggacgaaga gcatcagggg ctcgcgccag ccgaactgtt cgccaggctc aaggcgcgca    4920
tgcccgacgg cgaggatctc gtcgtgaccc atggcgatgc ctgcttgccg aatatcatgg    4980
tggaaaatgg ccgcttttct ggattcatcg actgtggccg gctgggtgtg gcggaccgct    5040
atcaggacat agcgttggct acccgtgata ttgctgaaga gcttggcggc gaatgggctg    5100
accgcttcct cgtgctttac ggtatcgccg ctcccgattc gcagcgcatc gccttctatc    5160
gccttcttga cgagttcttc tgagcgggac tctggggttc gaaatgaccg accaagcgac    5220
gcccaacctg ccatcacgag atttcgattc caccgccgcc ttctatgaaa ggttgggctt    5280
cggaatcgtt ttccgggacg ccggctggat gatcctccag cgcgggatc tcatgctgga    5340 gttcttcgcc caccccaact tgtttattgc agcttataat ggttacaaat aaagcaatag    5400
catcacaaat ttcacaaata aagcattttt tcactgcat tctagttgtg gtttgtccaa     5460
actcatcaat gtatcttatc atgtctgtat accgtcgacc tctagctaga gcttggcgta    5520
atcatggtca tagctgtttc ctgtgtgaaa ttgttatccg ctcacaattc cacacaacat    5580
acgagccgga agcataaagt gtaaagcctg gggtgcctaa tgagtgagct aactcacatt    5640
aattgcgttg cgctcactgc ccgctttcca gtcgggaaac ctgtcgtgcc agctgcatta    5700
```

```
atgaatcggc caacgcgcgg ggagaggcgg tttgcgtatt gggcgctctt ccgcttcctc    5760
gctcactgac tcgctgcgct cggtcgttcg gctgcggcga gcggtatcag ctcactcaaa    5820
ggcggtaata cggttatcca cagaatcagg ggataacgca ggaaagaaca tgtgagcaaa    5880
aggccagcaa aaggccagga accgtaaaaa ggccgcgttg ctggcgtttt tccataggct    5940
ccgcccccct gacgagcatc acaaaaatcg acgctcaagt cagaggtggc gaaacccgac    6000
aggactataa agataccagg cgtttccccc tggaagctcc ctcgtgcgct ctcctgttcc    6060
gaccctgccg cttaccggat acctgtccgc ctttctccct tcgggaagcg tggcgctttc    6120
tcatagctca cgctgtaggt atctcagttc ggtgtaggtc gttcgctcca agctgggctg    6180
tgtgcacgaa ccccccgttc agcccgaccg ctgcgcctta tccggtaact atcgtcttga    6240
gtccaacccg gtaagacacg acttatcgcc actggcagca gccactggta acaggattag    6300
cagagcgagg tatgtaggcg gtgctacaga gttcttgaag tggtggccta actacggcta    6360
cactagaaga acagtatttg gtatctgcgc tctgctgaag ccagttacct tcggaaaaag    6420
agttggtagc tcttgatccg gcaaacaaac caccgctggt agcggttttt tgtttgcaa    6480 gcagcagatt acgcgcagaa aaaaggatc tcaagaagat cctttgatct tttctacggg    6540
gtctgacgct cagtggaacg aaaactcacg ttagggggatt ttggtcatga gattatcaaa    6600
aaggatcttc acctagatcc ttttaaatta aaaatgaagt tttaaatcaa tctaaagtat    6660
atatgagtaa acttggtctg acagttacca atgcttaatc agtgaggcac ctatctcagc    6720
gatctgtcta tttcgttcat ccatagttgc ctgactcccc gtcgtgtaga taactacgat    6780
acgggagggc ttaccatctg gccccagtgc tgcaatgata ccgcgagacc cacgctcacc    6840
ggctccagat ttatcagcaa taaaccagcc agccggaagg gccgagcgca gaagtggtcc    6900
tgcaacttta tccgcctcca tccagtctat taattgttgc cgggaagcta gagtaagtag    6960
ttcgccagtt aatagtttgc gcaacgttgt tgccattgct acaggcatcg tggtgtcacg    7020
ctcgtcgttt ggtatggctt cattcagctc cggttcccaa cgatcaaggc gagttacatg    7080
atcccccatg ttgtgcaaaa aagcggttag ctccttcggt cctccgatcg ttgtcagaag    7140
taagttggcc gcagtgttat cactcatggt tatggcagca ctgcataatt ctcttactgt    7200
catgccatcc gtaagatgct tttctgtgac tggtgagtac tcaaccaagt cattctgaga    7260
atagtgtatg cggcgaccga gttgctcttg cccggcgtca atacgggata ataccgcgcc    7320
acatagcaga actttaaaag tgctcatcat tggaaaacgt tcttcgggc gaaaactctc    7380 aaggatctta ccgctgttga gatccagttc gatgtaaccc actcgtgcac ccaactgatc    7440
ttcagcatct tttactttca ccagcgtttc tgggtgagca aaaacaggaa ggcaaaatgc    7500
cgcaaaaaag ggaataaggg cgacacggaa atgttgaata ctcatactct ccttttttca    7560
atattattga agcatttatc agggttattg tctcatgagc ggatacatat ttgaatgtat    7620
ttagaaaaat aaacaaatag gggttccgcg cacatttccc cgaaaagtgc cacctgacgt    7680
c                                                                   7681
```

<210> SEQ ID NO 3
<211> LENGTH: 5181
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 3

-continued

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccag cccgtccagc agcaccatgt gggtgaccaa actcctgcca     780
gccctgctgc tgcagcatgt cctcctgcat ctcctcctgc tccccatcgc catccctat      840
gcagagggac aaaggaaaag aagaaataca attcatgaat tcaaaaaatc agcaaagact     900
accctaatca aaatagatcc agcactgaag ataaaaacca aaaagtgaa tactgcagac      960
caatgtgcta atagatgtac taggaataaa ggacttccat tcacttgcaa ggcttttgtt    1020
tttgataaag caagaaaaca atgcctctgg ttccccttca atagcatgtc aagtggagtg    1080
aaaaaagaat ttggccatga atttgacctc tatgaaaaca agactacat tagaaactgc     1140
atcattggta aaggacgcag ctacaaggga acagtatcta tcactaagag tggcatcaaa    1200
tgtcagccct ggagttccat gataccacac gaacacagct ttttgccttc gagctatcgg    1260
ggtaaagacc tacaggaaaa ctactgtcga atcctcgag gggaagaagg gggaccctgg     1320
tgtttcacaa gcaatccaga ggtacgctac gaagtctgtg acattcctca gtgttcagaa    1380
gttgaatgca tgacctgcaa tgggagagt tatcgaggtc tcatggatca tacagaatca     1440
ggcaagattt gtcagcgctg ggatcatcag acaccacacc ggcacaaatt cttgcctgaa    1500
agatatcccg acaagggctt tgatgataat tattgccgca atcccgatgg ccagccgagg    1560
ccatggtgct atactcttga ccctcacacc cgctgggagt actgtgcaat aaaacatgc     1620
gctgacaata ctatgaatga cactgatgtt cctttggaaa caactgaatg catccaaggt    1680
caaggagaag gctacagggg cactgtcaat accatttgga atggaattcc atgtcagcgt    1740
tgggattctc agtatcctca cgagcatgac atgactcctg aaaatttcaa gtgcaaggac    1800
ctacgagaaa attactgccg aaatccagat gggtctgaat caccctggtg ttttaccact    1860
gatccaaaca tccgagttgg ctactgctcc caaattccaa actgtgatat gtcacatgga    1920
caagattgtt atcgtgggaa tggcaaaaat tatatgggca acttatccca aacaagatct    1980
ggactaacat gttcaatgtg gacaagaac atggaagact acatcgtca tatcttctgg     2040
gaaccagatg caagtaagct gaatgagaat tactgccgaa atccagatga tgatgctcat    2100
ggaccctggt gctacacggg aaatccactc attccttggg attattgccc tatttctcgt    2160
tgtgaaggtg ataccacacc tacaatagtc aatttagacc atcccgtaat atcttgtgcc    2220
aaaacgaaac aattgcgagt tgtaaatggg attccaacac gaacaaacat aggatggatg    2280
gttagtttga gatacagaaa taaacatatc tgcggaggat cattgataaa ggagagttgg    2340
```

```
gttcttactg cacgacagtg tttcccttct cgagacttga aagattatga agcttggctt      2400
ggaattcatg atgtccacgg aagaggagat gagaaatgca aacaggttct caatgtttcc      2460
cagctggtat atggccctga aggatcagat ctggttttaa tgaagcttgc caggcctgct      2520
gtcctggatg attttgttag tacgattgat ttacctaatt atggatgcac aattcctgaa      2580
aagaccagtt gcagtgttta tggctggggc tacactggat tgatcaacta tgatggccta      2640
ttacgagtgg cacatctcta taatggga aatgagaaat gcagccagca tcatcgaggg       2700
aaggtgactc tgaatgagtc tgaaatatgt gctgggctg aaaagattgg atcaggacca      2760
tgtgagggga ttatggtgg cccacttgtt tgtgagcaac ataaaatgag aatggttctt       2820
ggtgtcattg ttcctggtcg tggatgtgcc attccaaatc gtcctggtat ttttgtccga      2880
gtagcatatt atgcaaaatg gatacacaaa attattttaa catataaggt accacagtca      2940
tagctgttaa cccgggtcga agcggccgct cgagtctaga gggcccgttt aaacccgctg      3000
atcagcctcg actgtgcctt ctagttgcca gccatctgtt gtttgcccct cccccgtgcc      3060
ttccttgacc ctggaaggtg ccactcccac tgtcctttcc taataaaatg aggaaattgc      3120
atcgcattgt ctgagtaggt gtcattctat tctgggggt ggggtggggc aggacagcaa       3180
gggggaggat tgggaagaca atagcaggca tgctgggat gcggtgggct ctatggcttc       3240
tactgggcgg ttttatggac agcaagcgaa ccggaattgc cagctgggc gccctctggt       3300 aaggttggga agccctgcaa agtaaactgg atggctttct gccgccaag gatctgatgg       3360 cgcagggat caagctctga tcaagagaca ggatgaggat cgtttcgcat gattgaacaa       3420
gatggattgc acgcaggttc tccggccgct tgggtggaga ggctattcgg ctatgactgg      3480
gcacaacaga caatcggctg ctctgatgcc gccgtgttcc ggctgtcagc gcaggggcgc      3540
ccggttcttt ttgtcaagac cgacctgtcc ggtgccctga atgaactgca agacgaggca      3600
gcgcggctat cgtggctggc cacgacgggc gttccttgcg cagctgtgct cgacgttgtc      3660
actgaagcgg gaagggactg gctgctattg ggcgaagtgc cggggcagga tctcctgtca      3720
tctcaccttg ctcctgccga gaaagtatcc atcatggctg atgcaatgcg gcggctgcat      3780
acgcttgatc cggctacctg cccattcgac caccaagcga aacatcgcat cgagcgagca      3840
cgtactcgga tggaagccgg tcttgtcgat caggatgatc tggacgaaga gcatcagggg      3900
ctcgcgccag ccgaactgtt cgccaggctc aaggcgagca tgcccgacgg cgaggatctc      3960
gtcgtgaccc atggcgatgc ctgcttgccg aatatcatgg tggaaaatgg ccgcttttct      4020
ggattcatcg actgtggccg ctgggtgtg gcggaccgct atcaggacat agcgttggct        4080
acccgtgata ttgctgaaga gcttggcggc gaatgggctg accgcttcct cgtgctttac      4140
ggtatcgccg ctcccgattc gcagcgcatc gccttctatc gccttcttga cgagttcttc      4200
tgaattatta cgcttacaa tttcctgatg cggtattttc tccttacgca tctgtgcggt        4260
atttcacacc gcatcaggtg gcacttttcg gggaaatgtg cgcggaaccc ctatttgttt      4320
atttttctaa atacattcaa atatgtatcc gctcatgaga caataaccct gataaatgct      4380
tcaataatag cacgtgctaa aacttcattt ttaatttaaa aggatctagg tgaagatcct      4440
ttttgataat ctcatgacca aaatccctta acgtgagttt tcgttccact gagcgtcaga      4500
ccccgtagaa aagatcaaag gatcttcttg agatcctttt tttctgcgcg taatctgctg      4560
cttgcaaaca aaaaaaccac cgctaccagc ggtggtttgt ttgccggatc aagagctacc      4620
aactcttttt ccgaaggtaa ctggcttcag cagagcgcag ataccaaata ctgttcttct      4680
agtgtagccg tagttaggcc accacttcaa gaactctgta gcaccgccta catacctcgc      4740
```

-continued

```
tctgctaatc ctgttaccag tggctgctgc cagtggcgat aagtcgtgtc ttaccgggtt    4800
ggactcaaga cgatagttac cggataaggc gcagcggtcg ggctgaacgg ggggttcgtg    4860
cacacagccc agcttggagc gaacgaccta caccgaactg agatacctac agcgtgagct    4920
atgagaaagc gccacgcttc ccgaagggag aaaggcggac aggtatccgg taagcggcag    4980
ggtcggaaca ggagagcgca cgagggagct tccaggggga aacgcctggt atctttatag    5040
tcctgtcggg tttcgccacc tctgacttga gcgtcgattt ttgtgatgct cgtcaggggg    5100
gcggagccta tggaaaaacg ccagcaacgc ggccttttta cggttcctgg cctttttgctg   5160 gccttttgct cacatgttct t                                              5181
```

HEPATOCYTE GROWTH FACTOR NUCLEIC ACID SEQUENCE TO ENHANCE MUSCULOCUTANEOUS FLAP SURVIVAL

BACKGROUND

1. Field of the Invention

This invention generally relates to the use of nucleic acid sequences encoding growth factors to promote angiogenesis and wound healing. In particular, described herein are methods and compositions for enhancing flap and skin graft survival by administering a nucleic acid sequence encoding hepatocyte growth factor.

2. Background of the Invention

Hepatocyte growth factor (HGF) functions as a growth factor for particular tissues and cell types. HGF was initially identified as a mitogen for hepatocytes. Michalopoulos et al., *Cancer Res.*, 44:4414-4419 (1984); Russel et al., *J. Cell. Physiol.*, 119:183-192 (1984); Nakamura et al., *Biochem. Biophys. Res. Comm.*, 122:1450-1459 (1984). Nakamura et al. (supra), reported the purification of HGF from the serum of partially hepatectomized rats. Subsequently, the subunit structure of HGF was determined when HGF was purified from rat platelets. Nakamura et al., *Proc. Natl. Acad. Sci. USA*, 83:6489-6493 (1986); Nakamura et al., *FEBS Letters*, 224:311-316 (1987). Human HGF ("huHGF") has also been purified from human plasma. Gohda et al., *J. Clin. Invest.*, 81:414-419 (1988).

Comparisons of the amino acid sequence of rat HGF and huHGF revealed that the two sequences are highly conserved and have the same characteristic structural features. For example, the length of the four kringle domains in rat HGF is exactly the same as in huHGF, and the location of cysteine residues are in exactly the same positions. This is an indication that the three-dimensional structure of the two proteins is similar. Okajima et al. *Eur. J. Bioch.*, 193:375-81 (1990); Tashiro et al., *Proc. Natl. Acad. Sci., USA*, 87:3200-4 (1990).

Furthermore, several reports revealed close sequence homology between HGF and scatter factor (SF). Gherardi and Stoker, *Nature*, 346:228 (1990); Weidner et al., *J. Cell Biol.*, 111:2097-2108 (1990); Coffer et al., *Biochem J.*, 278:35-41 (1991). SF is a polypeptide that stimulates dissociation of epithelial cell colonies in monolayer culture. Gherardi et al., *Proc. Natl. Acad. Sci. USA*, 86:5844-5848 (1989). In fact, there now is evidence indicating that the two factors are identical; they are identical in structure and biological activity. Weidner et al., *Proc. Natl. Acad. Sci. USA*, 88:7001-5 (1991); Bhargava et al., *Cell Growth Differ.* 3:11-20 (1992); Naldini et al., *EMBO J.*, 10:2867-78 (1991); Furlong et al., *J. Cell Sci.*, 100:173-7 (1991). HGF and HGF variants are described further in U.S. Pat. Nos. 5,227,158, 5,316,921, and 5,328,837.

Binding of HGF to its receptor is believed to be conveyed by a functional domain located in the N-terminal portion of the HGF molecule. Matsumoto et al., *Biochem. Biophys. Res. Commun.*, 181:691-699 (1991); Hartmann et al., *Proc. Natl. Acad. Sci. USA*, 89:11574-11578 (1992); Lokker et al., *EMBO J.*, 11:2503-2510 (1992); Lokker and Godowski, *J. Biol. Chem.*, 268:17145-17150 (1991). The HGF receptor is usually referred to as "c-Met" or "p$^{190}$MET" and typically comprises, in its native form, a 190-kDa heterodimeric (a disulfide-linked 50-kDa α-chain and a 145-kDa β-chain) membrane-spanning tyrosine kinase protein. Park et al., *Proc. Natl. Acad. Sci. USA*, 84:6379-6383 (1987). The c-Met protein becomes phosphorylated on tyrosine residues of the 145-kDa β-subunit upon HGF binding.

Various biological activities have been described for HGF and its receptor. See, generally, Chan et al., HEPATOCYTE GROWTH FACTOR—SCATTER FACTOR (HGF-SF) AND THE C-MET RECEPTOR, Goldberg and Rosen, eds., Birkhauser Verlag-Basel (1993), pp. 67-79). For example, HGF has been shown to be a mitogen for certain cell types, including melanocytes, renal tubular cells, keratinocytes, certain endothelial cells and cells of epithelial origin. Matsumoto et al., *Biochem. Biophys. Res. Commun.*, 176:45-51 (1991); Igawa et al., *Biochem. Biophys. Res. Commun.*, 174:831-838 (1991); Han et al., *Biochem.*, 30:9768-9780 (1991); Rubin et al., *Proc. Natl. Acad. Sci. USA*, 88:415-419 (1991). HGF has also been described as an epithelial morphogen, Montesano et al., *Cell*, 67:901-908 (1991), and therefore, HGF has been postulated to be important in tumor invasion, Comoglio, HEPATOCYTE GROWTH FACTOR—SCATTER FACTOR (HGF-SF) AND THE C-MET RECEPTOR, Goldberg and Rosen, eds., Birkhauser Verlag-Basel (1993), pp. 131-165. Until now, the intramuscular delivery of an HGF gene to promote flap and skin graft survival has not been described.

The use of skin flaps has gained increased acceptance and use in the course of reconstructive surgery, as well as in other forms of surgery. However, these techniques continue to be plagued by problems having to do with survival of the skin flaps which is, at least in part, due to the inefficient revascularization at the surgical site. Indeed, a number of approaches have been considered or evaluated for improving skin flap survival. See, for example, Waters et al., which provides a comparative analysis of the ability of five classes of pharmacological agents to augment skin flap survival in various models and species. *Annals of Plastic Surgery*, 23(2):117-22 (1989). Nevertheless, there still remains a need in the art for compositions and methods for enhancing survival of flap and skin grafts.

SUMMARY OF THE INVENTION

Therefore, the present invention describes the use of a nucleic acid sequence encoding HGF to enhance the survival of a flap or a skin graft.

In particular, described herein is a method for enhancing tissue survival, including survival of a flap or a skin graft following flap or skin graft surgery, comprising administering to a subject in need thereof a vector that comprises a nucleic acid sequence encoding hepatocyte growth factor. In specific embodiments, the vector is administered intramuscularly and is administered at least about 3-14 days prior to flap or skin graft surgery, at least about 5-10 days prior to surgery, or at least about 7 days prior to surgery. The instant invention is suitable for enhancing the survival of a flap, such as a skin flap, a muscle flap, a myocutaneous flap, or a cartilocutaneous flap, or a skin graft. Survival of the flap or skin graft may be enhanced by at least about 10-30% as compared to an untreated subject.

In one embodiment, the vector comprises the HGF nucleic acid sequence represented by SEQ ID NO. 1. The vector also may comprise the pcDNA3.1(−) plasmid, as set forth in SEQ ID NO. 2, or the pVAX1 plasmid, as set forth in SEQ ID NO. 3.

In another embodiment, the present invention discloses a method for enhancing organ transplant survival in a subject comprising administering to a subject in need thereof a therapeutically effective amount of a composition that comprises a nucleic acid sequence encoding HGF.

DETAILED DESCRIPTION OF THE INVENTION

1. Introduction

Figure 1:
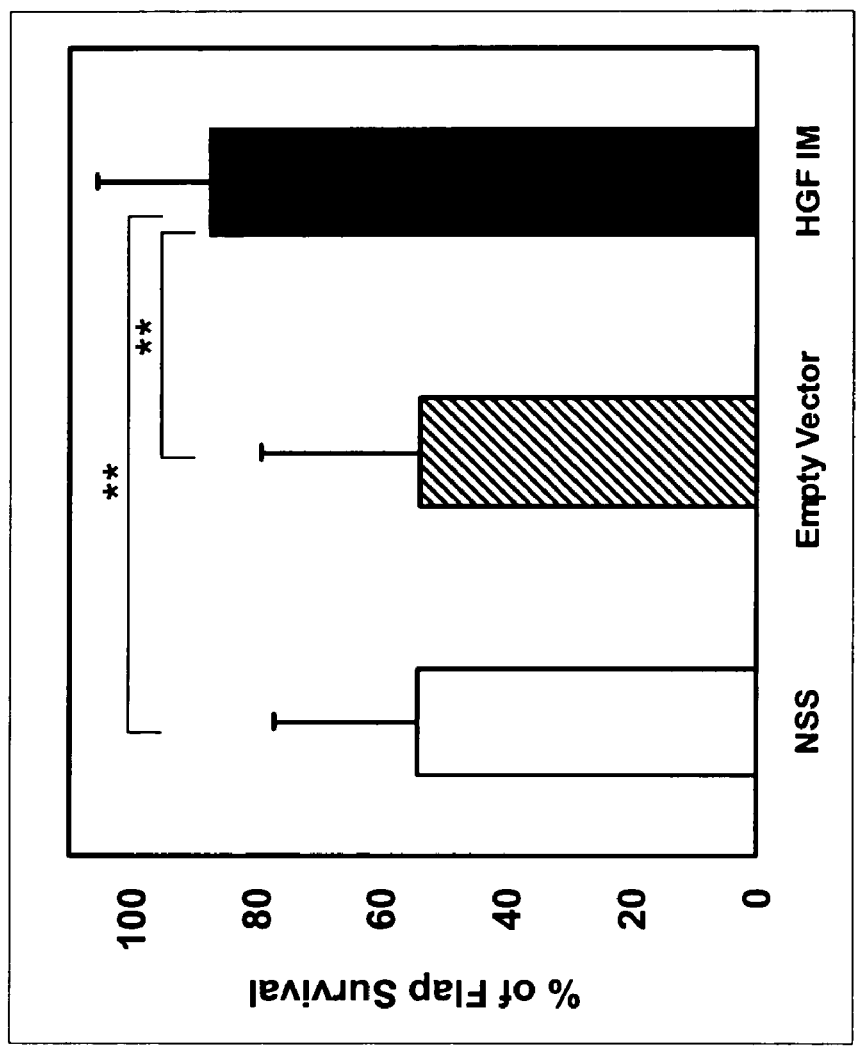
FIG. 1 compares musculocutaneous flap survival in an animal model after pretreatment with normal saline solution, an empty vector, or a vector comprising a nucleic acid sequence encoding HGF.

The inventors have surprisingly discovered that pre-treating subjects with a nucleic acid sequence encoding HGF prior to flap, skin graft or organ transplant surgery significantly enhances survival of the tissue as compared to transplanted tissue in control subjects.

2. Definitions

Unless otherwise specified, "a" or "an" means one or more.

The terms "hepatocyte growth factor" and "HGF" as used herein include hepatocyte growth factor from humans ("hu-HGF") and any non-human mammalian species of HGF, including rat HGF. The term "HGF" as used herein includes mature, pre, pre-pro, and pro forms, including forms purified from a natural source, and chemically synthesized or recombinantly produced HGF.

"Sequence identity" is defined herein with reference the Blast 2 algorithm, which is available at the NCBI (http://www.ncbi.nlm.nih.gov/BLAST), using default parameters. References pertaining to this algorithm include those found at http://www.ncbi.nlm.nih.gov/BLAST/blast_references.html; Altschul, et al., J. Mol. Biol. 215: 403-410 (1990); Gish & States, Nature Genet. 3: 266-272 (1993); Madden et al., Meth. Enzymol. 266: 131-141 (1996); Altschul et al., Nucleic Acids Res. 25: 3389-3402 (1997), and Zhang & Madden, Genome Res. 7: 649-656 (1997).

The terms "alteration," "amino acid alteration," "variant," and "amino acid sequence variant" refer to HGF molecules with some differences in their amino acid sequences as compared to a native human HGF. Ordinarily, the variants will possess at least about 80%, 85%, or 90% homology with the domains of native human HGF, including sequences at least about 95% homologous or at least about 99% homologous to native human HGF.

3. Hepatocyte Growth Factor Nucleic Acid Sequence and Variants Thereof

The nucleic acid sequences encoding HGF for use in the present invention may encode a hepatic parenchymal cell growth factor. The encoded HGF may have a structure with six domains (finger, Kringle 1, Kringle 2, Kringle 3, Kringle 4 and serine protease domains).

One human HGF nucleic acid sequence suitable for use in the present invention is represented as SEQ ID NO:1 herein.

Other human HGF nucleic acids also are suitable for use in the present invention, such as the hepatic parenchymal cell growth factor sequence disclosed in Kitamura et al., U.S. Pat. No. 5,500,354.

Likewise, non-mammalian HGF nucleic acids are suitable for use in the present invention. Rat HGF, for example, shares the same structural features as human HGF and is described in Tashiro et al., Proc. Nat'l. Acad. Sci. USA, 87(8):3200-4 (1990) and GenBank Accession No. NM_017017.

In other embodiments, the nucleic acid encoding HGF useful in the present invention has at least about 80% sequence identity, at least about 85% sequence identity, at least about 90% sequence identity, at least about 95% sequence identity, or at least 99% sequence identity with a native mammalian HGF gene. For example, genes having at least about 80% sequence identity, at least about 85% sequence identity, at least about 90% sequence identity, at least about 95% sequence identity, or at least about 99% sequence identity to SEQ ID NO:1 can be used in the present invention. As used herein, two nucleic acid molecules or proteins are said to "share significant sequence identity" if the two contain regions which possess greater than 90% sequence (amino acid or nucleic acid) identity over the entire length of the gene.

The invention also includes nucleic acid sequences that encode HGF proteins that are variants of a native HGF protein. For example, such HGF variants may have at least about 80% sequence identity, at least about 85% sequence identity, at least about 90% identity, at least 95% identity, or at least about 99% sequence identity to the protein encoded by the nucleic acid sequence represented in SEQ ID NO. 1. Given the known genetic code, and recombinant and synthetic DNA techniques, the skilled scientist readily can construct DNAs encoding the conservative amino acid variants described herein. Examples of suitable variants are described below.

Fragments of HGF constitute HGF with fewer than all six domains (finger, Kringle 1, Kringle 2, Kringle 3, Kringle 4 and serine protease domains). Variants of HGF may have some of the domains of HGF repeated. Both fragments and variants are included within the scope of the invention if they still retain their respective ability to bind a HGF receptor, as determined by means known in the art.

Substituted HGF variants are those that have at least one amino acid residue in the corresponding wild-type HGF sequence removed and a different amino acid inserted in its place at the same position. The substitutions may be single, where only one amino acid in the molecule has been substituted, or they may be multiple, where two or more amino acids have been substituted in the same molecule. Conservative substitutions are contemplated in the present invention. For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid, and substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I.

Insertional HGF variants are those with one or more amino acids inserted immediately adjacent to an amino acid at a particular position in the wild-type HGF molecule. Immediately adjacent to an amino acid means connected to either the α-carboxy or α-amino functional group of the amino acid. The insertion may be of one or more amino acids. Ordinarily, the insertion will consist of one or two conservative amino acids. As stated above, amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the wild-type HGF molecule removed. Ordinarily, deletional variants will have one or two amino acids deleted in a particular region of the HGF molecule. Such deletional variants are also contemplated in the present invention.

All variants suitable for use in the present invention retain HGF activity. Such activity can be assayed by one of skill in the art according to known methods.

4. Recombinant Vector Production

Recombinant vector production is well known in the art and is outlined in a brief exemplary fashion below.

Generally speaking, the constructs of the present invention comprise a vector, such as a plasmid or viral vector, into which a genomic DNA or DNA fragment or cDNA bearing an open reading frame is inserted, in either orientation. The invention further contemplates cells containing these vectors.

Bacterial Expression

Useful vectors for bacterial expression may be constructed by inserting a structural DNA sequence encoding a desired protein, together with suitable translation initiation and termination signals in operable reading phase with a functional promoter. The vector may comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. In one embodiment, the prokaryotic host is *E. coli*.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, pGEM 1 (Promega Biotec, Madison, Wis., USA), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia).

These "backbone" sections may be combined with an appropriate promoter and the structural sequence to be expressed. Bacterial promoters include lac, T3, T7, lambda $P_R$ or $P_L$, trp, and ara.

These vectors optionally may be used for recombinant protein production. Following transformation of a suitable host strain and growth of the host strain to an appropriate cell density, the selected promoter may be derepressed/induced by appropriate means (e.g., temperature shift or chemical induction) and cells may be cultured for an additional period. Cells are typically harvested by centrifugation, disrupted by physical or chemical means, and the resulting crude extract retained for further purification and isolation of the recombinant protein.

Eukaryotic Expression Vectors

In one embodiment, HGF cDNA is subcloned into a mammalian expression vector. Various mammalian cell culture systems can be employed to express recombinant protein. Examples of mammalian expression systems include selected mouse L cells, such as thymidine kinase-negative (TK) and adenine phosphoribosyl transferase-negative (APRT) cells. Other examples include the COS-7 lines of monkey kidney fibroblasts, described by Gluzman, *Cell* 23: 175 (1981), and other cell lines capable of expressing a compatible vector, for example, the C127, 3T3, CHO, HeLa and BHK cell lines. Mammalian expression vectors may comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-I. In one embodiment, the HGF cDNA is subcloned into any expression vector in which the expression is driven by a CMV promoter. Exemplary mammalian vectors include pWLneo, pSV2cat, pOG44, pXT1, pSG (Stratagene) pSVK3, pBPV, pMSG, and pSVL (Pharmacia). In one specific embodiment, the mammalian expression vector is pcDNA3.1 (Invitrogen) or pVAX1 (Invitrogen). pVAX1 is a 3.0 kb plasmid vector designed for use in the development of DNA vaccines. HGF cDNA can be inserted, for example, into a multiple cloning site of the pVAX1 vector. pcDNA3.1(−) has the same multiple cloning site as pcDNA3.1(+) but in a reverse orientation.

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (See, e.g., Logan et al., 1984, *Proc. Natl. Acad. Sci. USA* 81: 3655-3659). If a viral vector is chosen as the delivery vehicle it may be one which is capable of integrating into the host genome so that the gene can be expressed permanently. In cases where the vector does not integrate into the host genome, the expression of the gene may be transient rather than permanent.

Adenoviral vectors ("Ad") are currently among the most efficient gene transfer vehicles for both in vitro and in vivo delivery, but the utilization of a first generation Ad for many gene therapy applications is limited due to the transient nature of transgene expression obtained by these vectors. Several factors have been shown to contribute to and modulate the duration of Ad-mediated gene expression as well as the immunogenicity of these vectors, including "leaky" viral protein expression and the transgene delivered. The development of Ad vectors, deleted in all viral protein coding sequences offers the prospects of a potentially safer, less immunogenic vector with an insert capacity of up to approximately 37 kb.

This vector requires supplementation of viral regulatory and structural proteins in trans for packaging and rescue and is therefore helper dependent (HD). This is further described in Parks et al., *Proc. Natl. Acad. Sci. USA*, 93:13565-13570 (1996).

Use of retroviral vectors for protein expression are also known in the art. See, for example, Veres, et al., *J. Virol.*, 72:1894-1901 (1998); Agarwal et al., *J. Virol.*, 72:3720-3728 (1998); Forestell et al., *Gene Therapy*, 4:600-610 (1997); Plavec et al., *Gene Therapy*, 4:128-139, 1997; Forestell et al., *Gene Therapy*, 2:723-730 (1995); and Rigg et al., *J. Virol.*, 218:290-295, 1996. The genome of a recombinant retroviral vector is comprised of long terminal repeat (LTR) sequences at both ends which serve as a viral promoter/enhancer and a transcription initiation site, and a Psi site which serves as a virion packaging signal and a selectable marker gene. In one embodiment, the HGF polynucleotide sequences disclosed herein can be cloned into a suitable cloning site in the retroviral genome. Expression is under the transcriptional control of the retroviral LTR. Tissue selectivity is determined by both the origin of the viral genome (e.g., sarcoma virus, leukemia virus, or mammary tumor virus) and the cell line used to package the virus.

The recombinant vector useful in the present invention may include the exogenous DNA and regulatory sequences necessary and sufficient for expression of the encoded product (e.g., HGF) upon entry into the target cell. In one embodiment of the present invention, the vector includes exogenous DNA encoding the desired product (i.e., HGF), and, optionally, DNA encoding a selectable marker, along with additional sequences necessary for expression of the exogenous DNA in a target cell. In one specific embodiment, the vector comprises the nucleic acid sequence of SEQ ID NO. 1 and a pcDNA3.1(−) plasmid or a pVAX1 plasmid is used. See, e.g., SEQ ID NOs. 2 and 3. In yet another embodiment, the vector does not comprise an enhancer element. Additionally, infectious vectors can be used in the present invention, such as adenoviral, retroviral, and adenovirus-associated viral vectors, to express the exogenous DNA sequence in a target cell.

In accordance with the invention, a vector encoding HGF may be administered by intramuscular injection, or by intravenous, intraperitoneal, oral or subcutaneous means, or by other means of delivery. Suitable titers will depend on a number of factors, such as the particular vector chosen, the host, and the strength of promoter used.

In accordance with the invention, the vector encoding HGF is administered (for example, by intramuscular injection) prior to organ transplant, skin flap or skin graft surgery, up to a week or more prior to surgery. Administration at least about 3 days, at least about 4 days, at least about 5 days, at least about 6 days, at least about 7 days, at least about 8 days, at least about 9 days, or at least about 10 days prior to organ transplant or flap or skin graft surgery is expressly contemplated and included within the invention. Administration up to about 14 days prior to organ transplant or flap or skin graft surgery is also contemplated and included within the invention. The term "about" in this context connotes up to one day before the specified number of days. For example, the phrase "at least about 3 days" means that the construct encoding HGF is administered between 2-3 days prior to organ transplant or flap or skin graft surgery. Thus, 2, 4, 6, 8, 10, 12, 14, 16, 18, 20, 22 or 24 hours prior to precisely 3 days before the surgery is within the meaning of the term "about."

Administration of the vector encoding HGF may be by direct injection, i.e., at or near the site of the flap, graft or organ transplant. In one embodiment, the construct encoding HGF is administered intramuscularly, such into the rectus abdominus muscle.

The inventive methods described herein enhance flap or skin graft survival by at least about 10%, at least about 15%, at least about 20%, at least about 25%, or at least about 30% or more compared to an untreated control subject. The term "about" in this context connotes a range of up to 5% before or after the specified percentage. Thus, the phrase "about 10%" refers to a range of 5%-15%, but also specifically includes 10%.

5. Pharmaceutically Acceptable Formulations

The HGF vector or HGF nucleic acid sequence compositions as described herein can be formulated according to known methods to prepare pharmaceutically useful compositions, whereby the inventive compositions, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). To form a pharmaceutically acceptable composition suitable for effective administration, such compositions will contain an effective amount of one or more of the vectors of the present invention, together with a suitable amount of carrier vehicle.

Pharmaceutical compositions for use in accordance with the present invention may be formulated in conventional manner using one or more physiologically acceptable carriers or excipients. Thus, the HGF vector or HGF nucleic acid sequence compositions described herein, and their physiologically acceptable salts and solvate, may be formulated for administration by inhalation or insufflation (either through the mouth or the nose) or oral, buccal, rectal, subcutaneous or intramuscular administration. In one embodiment, the HGF nucleic acid sequence or HGF vector compositions are formulated for intramuscular administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the composition may take the form of tablets or lozenges formulated in conventional manner.

For administration by inhalation, the HGF vector or HGF nucleic acid sequence compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The HGF vector or HGF nucleic acid sequence compositions may be formulated for intravenous, subcutaneous or intramuscular administration by injection, e.g., by bolus injection or continuous infusion. Formulations for injection may be presented in unit dosage form, e.g., in ampules or in multi-dose containers, with an added preservative. The HGF compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the HGF vector or HGF nucleic acid sequence compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention describes therapy with HGF nucleic acid sequences to enhance organ transplant, flap and skin graft survival. In particular, a nucleic acid sequence encoding HGF can be administered prior to organ transplant, flap or skin graft surgery. The invention is useful in any type of organ transplant, flap or skin graft surgery. For example, the invention is useful in conjunction with transplantation of a wide variety of organs, including skin, kidney, heart, liver, spleen, bone marrow, pancreas, lung, and islet of langerhans. There are many different kinds of flaps that can be used to address cutaneous defects, defects of muscle, defects of subcutaneous tissues, and defects in bone. For example, the HGF methods and compositions of the present invention can be used in conjunction with (including prior to) a cutaneous flap, muscle flap, myocutaneous flap, or cartilocutaneous flap surgery. Likewise, the HGF methods and compositions of the present invention can be used in conjunction with (including prior to) skin graft surgery.

The therapeutic methods of the present invention involve administering to a subject in need of treatment a therapeutically effective amount of the HGF vector or HGF nucleic acid sequence compositions described herein. "Therapeutically effective" is employed here to denote the amount of the HGF composition that is of sufficient quantity to promote angiogenesis and accelerate wound healing. In particular, it is desirable to administer a therapeutically effective amount of an HGF composition that will enhance organ transplant, musculocutaneous flap or skin graft survival. Some methods contemplate combination therapy with known medicaments or therapies that also promote angiogenesis or organ or flap survival.

The therapeutically effective amount of the HGF composition for use in this invention largely will depend on particular patient characteristics, the route of administration, and the nature of the disorder being treated (such as the type of organ transplant or the size, location, and thickness of the flap or skin graft at issue). General guidance can be found, for example, in the publications of the International Conference on Harmonisation and in REMINGTON'S PHARMACEUTICAL SCIENCES, chapters 27 and 28, pp. 484-528 (Mack Publishing Company 1990). In addition, the therapeutically effective amount may depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the decrease in necrosis, or the increase in angiogenesis or organ transplant or flap or graft survival. As illustrated by the foregoing references, the determination of a therapeutically effective amount can be determined by those skilled in the art, as guided by this disclosure.

In one embodiment, the therapeutically effective amount is from about 0.1 to about 50 mg per treatment, such as from about 0.5 to about 25 mg per treatment, and from about 1 to about 10 mg per treatment. In a specific embodiment, the plasmid is administered in several injections to the same area of the body as part of a single treatment.

The patient may be a human or non-human mammal, or another animal. A patient typically will be in need of treatment when scheduled to receive flap or skin graft surgery.

The invention is further described by reference to the following examples, which are provided for illustration only. The invention is not limited to the examples but rather includes all variations that are evident from the teachings provided herein.

EXAMPLE 1

Plasmid Constructs

Human HGF is subcloned into the pcDNA3.1(−) (Invitrogen) into the NotI site, which produces the human HGF protein under the control of the CMV promoter. See, e.g., SEQ ID NO. 2. The HGF gene plasmid concentrate is reconstituted with normal saline solution (NSS) to obtain a 1 μg/μl concentration.

EXAMPLE 2

HGF Nucleic Acid Sequence Enhances Flap Survival

The experiment is conducted following the guidelines set by the animal laboratory of the Institute of Animal and Experimental Sciences, Osaka University. Twenty four male Sprague-Dawley rats weighing 300-350 grams are used and equally divided into three groups (N=8). Animals are anesthetized with an intraperitoneal injection of pentobarbital (2 mg/100 g). In group 1, 250 μl of NSS is injected into the left rectus abdominus muscle, while 250 μg (1 μg/μl) of empty plasmid (pcDNA3.1(−)) and 250 μg (1 μg/μl) of HGF gene containing plasmid is injected into the same site in Group 2 and Group 3, respectively. After 7 days, a simulated transverse rectus abdominus musculocutaneous (TRAM) flap measuring 4.5 cm×9 cm is elevated. TRAM flap based on the left rectus abdominus muscle as the carrier and the superior epigastric vessels as the vascular pedicle are designed on the lower half of the abdomen. The flap is sutured to its original location and monitored for 1 week for infection, necrosis and flap survival. All the animals are sacrificed using an overdose of pentobarbital given intraperitonally. Direct measurement is made on the area of necrosis and flap survival using a transparent metric template.

The data indicate the following with regard to flap survival one week post-surgery:

TABLE 1

|  | NSS | Empty Vector | HGF IM |
|---|---|---|---|
| % Flap Survival | 54.125 | 53.875 | 87.75 |
| Standard Deviation | 22.96853438 | 25.41336825 | 17.88654722 |
| Sample Size | 8 | 8 | 8 |

Figure 2:
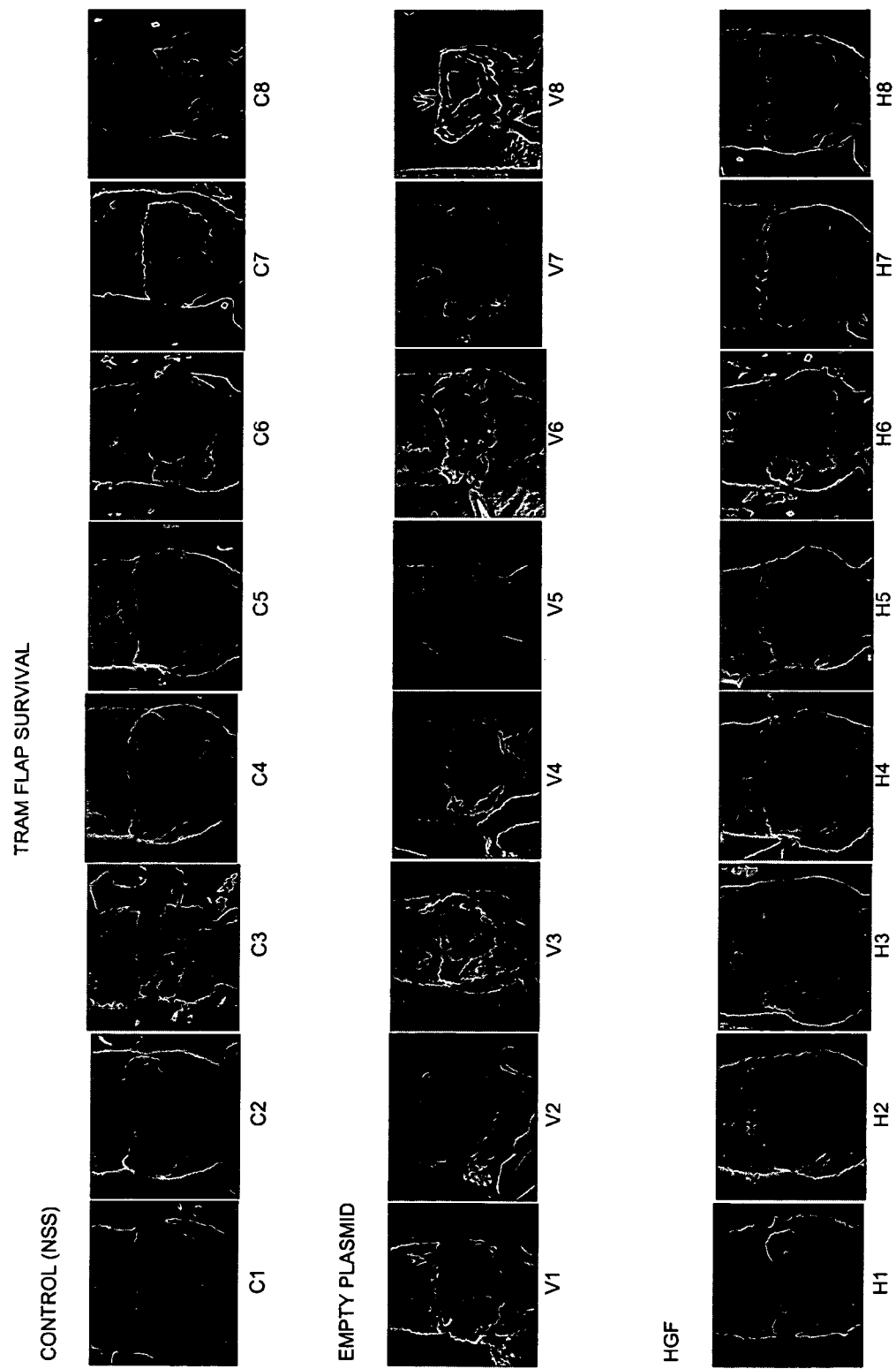
FIG. 2 depicts the survival (1 week after surgery) of a transverse rectus abdominis musculocutaneous (TRAM) flap in rats pre-treated 7 days prior to the surgery with (A) normal saline, (B) empty vector or (C) vector comprising a nucleic acid sequence encoding HGF. (N=8 for each group).

The superiority of pre-treating a TRAM flap with a gene encoding HGF is also exemplified in FIG. 2. FIG. 2 demonstrates that flap survival is markedly enhanced one week post-surgery in animals receiving a gene encoding HGF (designated as "H" animals; n=8) at least 7 days prior to flap surgery, compared to control animals (designated as "C" animals; n=8) and animals treated with the empty vector (designated as "V" animals; n=8). (The number following the letters "H," "C" or "V" indicate the animal number.)

In a separate study, 20 Sprague Dawley rats were randomized into 5 groups, 4 rats per group, and were directly injected with 125 μg, 250 μg, or 500 μg of a plasmid encoding HGF, NSS, or an empty vector into the left rectus abdominus muscle, (the likely TRAM flap cite). One week post-injection, skin blood flow measurements were taken by a laser color Doppler (Laser Doppler Imager, Moor Instruments), which determines blood flow velocity and correlates with capillary density. The results indicated that blood flow was higher in the treated area for the HGF treated groups compared to the groups given NSS or the empty vector (FIG. 3 and Table 2).

TABLE 2

|  | NSS | Empty Vector | HGF IM (125 μg) | HGF IM (250 μg) | HGF IM (500 μg) |
|---|---|---|---|---|---|
| Mean % Blood Flow | 282.675 | 278.175 | 343.333 | 392.900 | 396.725 |
| Standard Error | 5.923593 | 16.7246 | 15.59202 | 37.70972 | 33.55604 |
| Sample Size | 4 | 4 | 4 | 4 | 4 |

Figure 3:
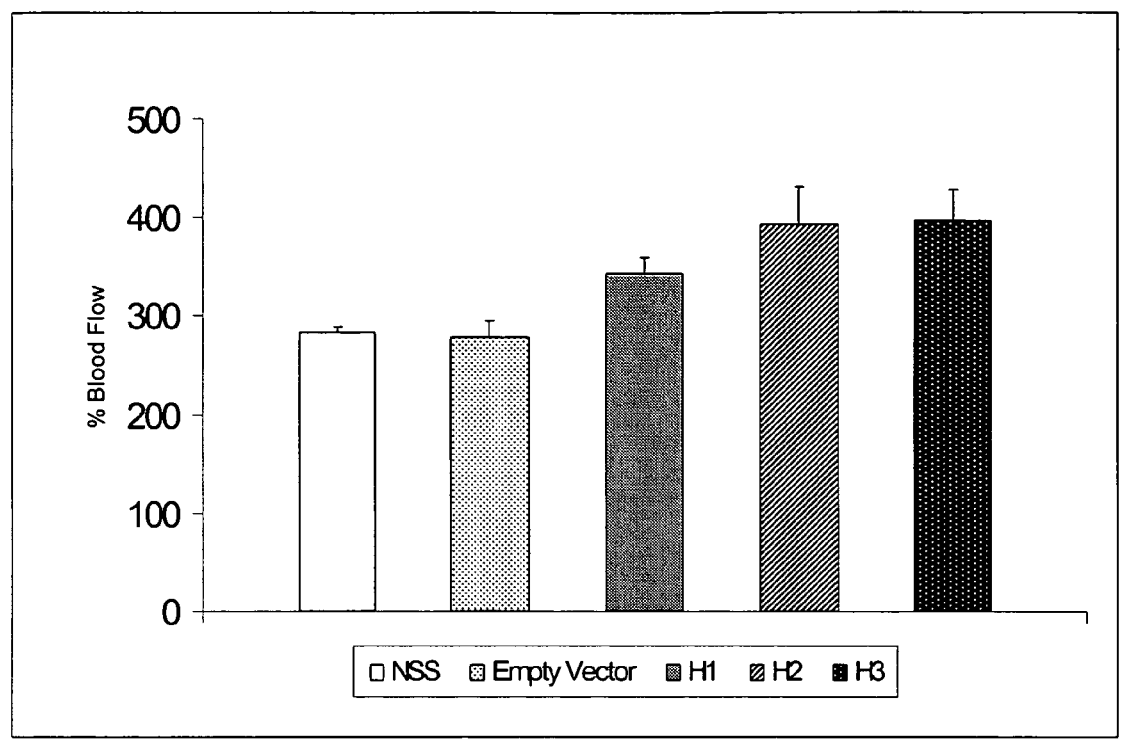
FIG. 3 is a histogram representing mean percentage blood flow in animals given normal saline solution (NSS), empty vector, or a vector comprising a nucleic acid sequence encoding HGF one week post-injection. Groups H1, H2 and H3 represent the experimental groups treated with 125 µg, 250 µg, and 500 µg HGF, respectively.

FIG. 3 was generated by quantitatively converting the laser images from the laser Doppler, creating a histogram with the amount of blood flow provided on the y-axis and each experimental group, i.e., animals given NSS, the empty vector, H1(125 μg HGF), H2 (250 μg HGF) or H3 (500 μg HGF), on the x-axis. Use of the laser Doppler to visualize blood vessels and measure blood flow is described in Wong et al., Gastrointest. Endosc., 55(1): 88-95 (2002).

Additional embodiments are within the scope of the invention. For example, the invention is further illustrated by the following numbered embodiments:

1. A method for enhancing tissue survival, including survival of a flap or a skin graft following flap or skin graft surgery, comprising administering to a subject in need thereof a vector that comprises a nucleic acid sequence encoding hepatocyte growth factor.

2. The method of embodiment 1, wherein said flap is selected from the group consisting of a skin flap, a muscle flap, a myocutaneous flap and a cartilocutaneous flap.

3. The method of embodiment 1, wherein said vector is administered intramuscularly.

4. The method of embodiment 1, wherein said nucleic acid encoding HGF is represented by SEQ ID NO. 1.

5. The method of embodiment 4, wherein said vector is administered at least 3-14 days prior to flap or skin graft surgery.

6. The method of embodiment 4, wherein said vector is administered at least 5-10 days prior to flap or skin graft surgery.

7. The method of embodiment 4, wherein said vector is administered at least 7 days prior to flap or skin graft surgery.

8. The method of embodiment 5, wherein said vector is a plasmid selected from the group consisting of pcDNA3.1(−) and pVAX1.

9. The method of embodiment 5, wherein said vector comprises the sequence of SEQ ID NO. 2.

10. The method of embodiment 5, wherein said vector comprises sequence of SEQ ID NO. 3.

11. The method of embodiment 1, wherein the survival of the flap or skin graft is enhanced by at least 10-30% as compared to an untreated subject.

12. A method for enhancing organ transplant survival in a subject comprising administering to a subject in need thereof a therapeutically effective amount of a composition that comprises a nucleic acid encoding HGF.

13. The method of embodiment 3, wherein said vector is administered in the rectus abdominus muscle.

14. A method for enhancing tissue survival, including survival of a flap or a skin graft following flap or skin graft surgery, comprising administering to a subject in need thereof a vector that comprises a nucleic acid sequence encoding hepatocyte growth factor, wherein administration of the vector results in enhanced blood flow.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited in this specification are incorporated herein by reference in their entirety.

Hepatocyte Growth Factor Nucleic Acid Sequence
SEQ ID NO. 1
ATGTGGGTGACCAAACTCCTGCCAGCCCTGCTGCTGCAGCATGTCCTCCT

GCATCTCCTCCTGCTCCCCATCGCCATCCCCTATGCAGAGGGACAAAGGA

AAAGAAGAAATACAATTCATGAATTCAAAAAATCAGCAAAGACTACCCTA

ATCAAAATAGATCCAGCACTGAAGATAAAAACCAAAAAAGTGAATACTGC

AGACCAATGTGCTAATAGATGTACTAGGAATAAAGGACTTCCATTCACTT

GCAAGGCTTTTGTTTTTGATAAAGCAAGAAAACAATGCCTCTGGTTCCCC

-continued

TTCAATAGCATGTCAAGTGGAGTGAAAAAAGAATTTGGCCATGAATTTGA

CCTCTATGAAAACAAAGACTACATTAGAAACTGCATCATTGGTAAAGGAC

GCAGCTACAAGGGAACAGTATCTATCACTAAGAGTGGCATCAAATGTCAG

CCCTGGAGTTCCATGATACCACACGAACACAGCTTTTTGCCTTCGAGCTA

TCGGGGTAAAGACCTACAGGAAAACTACTGTCGAAATCCTCGAGGGGAAG

AAGGGGGACCCTGGTGTTTCACAAGCAATCCAGAGGTACGCTACGAAGTC

TGTGACATTCCTCAGTGTTCAGAAGTTGAATGCATGACCTGCAATGGGGA

GAGTTATCGAGGTCTCATGGATCATACAGAATCAGGCAAGATTTGTCAGC

GCTGGGATCATCAGACACCACACCGGCACAAATTCTTGCCTGAAAGATAT

CCCGACAAGGGCTTTGATGATAATTATTGCCGCAATCCCGATGGCCAGCC

GAGGCCATGGTGCTATACTCTTGACCCTCACACCCGCTGGGAGTACTGTG

CAATTAAAACATGCGCTGACAATACTATGAATGACACTGATGTTCCTTTG

GAAACAACTGAATGCATCCAAGGTCAAGGAGAAGGCTACAGGGGCACTGT

CAATACCATTTGGAATGGAATTCCATGTCAGCGTTGGGATTCTCAGTATC

CTCACGAGCATGACATGACTCCTGAAAATTTCAAGTGCAAGGACCTACGA

GAAAATTACTGCCGAAATCCAGATGGGTCTGAATCACCCTGGTGTTTTAC

CACTGATCCAAACATCCGAGTTGGCTACTGCTCCCAAATTCCAAACTGTG

ATATGTCACATGGACAAGATTGTTATCGTGGGAATGGCAAAAATTATATG

GGCAACTTATCCCAAACAAGATCTGGACTAACATGTTCAATGTGGGACAA

-continued

GAACATGGAAGACTTACATCGTCATATCTTCTGGGAACCAGATGCAAGTA

AGCTGAATGAGAATTACTGCCGAAATCCAGATGATGATGCTCATGGACCC

TGGTGCTACACGGGAAATCCACTCATTCCTTGGGATTATTGCCCTATTTC

TCGTTGTGAAGGTGATACCACACCTACAATAGTCAATTTAGACCATCCCG

TAATATCTTGTGCCAAAACGAAACAATTGCGAGTTGTAAATGGGATTCCA

ACACGAACAAACATAGGATGGATGGTTAGTTTGAGATACAGAAATAAACA

TATCTGCGGAGGATCATTGATAAAGGAGAGTTGGGTTCTTACTGCACGAC

AGTGTTTCCCTTCTCGAGACTTGAAAGATTATGAAGCTTGGCTTGGAATT

CATGATGTCCACGGAAGAGGAGATGAGAAATGCAAACAGGTTCTCAATGT

TTCCCAGCTGGTATATGGCCCTGAAGGATCAGATCTGGTTTTAATGAAGC

TTGCCAGGCCTGCTGTCCTGGATGATTTTGTTAGTACGATTGATTTACCT

AATTATGGATGCACAATTCCTGAAAAGACCAGTTGCAGTGTTTATGGCTG

GGGCTACACTGGATTGATCAACTATGATGGCCTATTACGAGTGGCACATC

TCTATATAATGGGAAATGAGAAATGCAGCCAGCATCATCGAGGGAAGGTG

ACTCTGAATGAGTCTGAAATATGTGCTGGGGCTGAAAAGATTGGATCAGG

ACCATGTGAGGGGATTATGGTGGCCCACTTGTTTGTGAGCAACATAAAA

TGAGAATGGTTCTTGGTGTCATTGTTCCTGGTCGTGGATGTGCCATTCCA

AATCGTCCTGGTATTTTTGTCCGAGTAGCATATTATGCAAAATGGATACA

CAAAATTATTTTAACATATAAGGTACCACAGTCATAG pcDNA3.1(-) HGF Sequence                                                                                                               SEQ ID NO. 2

| | | | | | | | |
|---|---|---|---|---|---|---|---|
| GACGGATCGG | GAGATCTCCC | GATCCCCTAT | AACATATCTG | CGGAGGATCA | TTGATAAAGG | TCTTACTGCA | CGACAGTGTT | CTTGTGTGTT |
| GGAGTCGCT | GAGTAGTGCG | CGAGCAAAG | AATTCATGAT | GTCCACGGAA | GAGGAGATGA | CAGTTCTCA | ATGTTTCCA | GCGTTTGCG |
| CTGCTTCGCG | ATGTACGGGC | CAGATATACG | AAGCTTGCCA | GGCTGCTGT | CTTGTTAGTA | CGATTGATTT | ACCTAATTAT | AGCCCATATA |
| TGGAGTTCCG | CGTTACATAA | CTTACGTAA | AGTGTTTATG | CACTGGATG | ATCAACTATG | ACGAGTCAGT | CATCTGATTT | TTCCCATAGT |
| AACGCCAATA | GGGACTTTCC | ATTGACGTCA | ATGGGTGGAG | GGTGACTCTG | AAATATGTGC | AAGACCATG | CAGGACCATG | AAGTACGCCC |
| CCTATTGACG | TCAATGACGG | TAAATGGCCC | GCCTGGCATT | ATGCCCAGTA | TGTCATTTT | GATGTGCCAT | TCCAAATGT | GTATTAGTCA |
| TCGCTATTAC | CATGGTGATG | CGGTTTTGGC | AGTACATCAA | TGGGCGTGGA | TAGCGGTTTG | ACTCACGGGGG | ATTCCAAGT | TTGACGTCAA |
| TGGGAGTTTG | TTTTGGCACC | AAAATCAACG | GGACTTTCCA | AAATGTCGTA | ACAACTCCGC | CCCATTGACG | CAAATGGGCG | GTAGGCGTGT |
| ACGGTGGGAG | GTCTATATAA | GCAGAGCTC | TCTGGCTAAC | TAGAGAACCA | CTGCTTACTG | GCTTATCGAA | ATTAATACGA | CTCACTATAG |
| GGAGACCCAA | GCTGGCTAGC | GTTTAAACTT | AAGCTTGGTA | CCGAGCTCGG | ATCCACTAGT | CCAGTGTGGT | GGAATTCTGC | AGATATCCAG |
| CACACTGGCG | GCCGTTACTA | GTGGATCCGA | GCTCGGTACC | AAGCTTAAGT | TTAAACCGCT | GATCAGCCTC | GACTGTGCCT | TCTAGTTGCC |
| AGCCATCTGT | TGTTTGCCCC | TCCCCCCGTG | CCTTCCTTGA | CCCTGGAAGG | TGCCACTCCC | ACTGTCCTTT | CCTAATAAAA | TGAGGAAATT |
| GCATCGCATT | GTCTGAGTAG | GTGTCATTCT | ATTCTGGGGG | GTGGGGTGGG | GCAGGACAGC | AAGGGGAGGAT | TGGGAAGACA | ATAGCAGGCA |
| TGCTGGGGAT | GCGGTGGGCT | CTATGGCTTC | TGAGGCGGAA | AGAACCAGCT | GGGGCTCTAG | GGGGTATCCC | CACGCGCCCT | GTAGCGGCGC |
| ATTAAGCGCG | GCGGGTGTGG | TGGTTACGCG | CAGCGTGACC | GCTACACTTG | CCAGCGCCCT | AGCGCCCGCT | CCTTTCGCTT | TCTTCCCTTC |
| CTTTCTCGCC | ACGTTCGCCG | GCTTTCCCCG | TCAAGCTCTA | AATCGGGGGC | TCCCTTTAGG | GTTCCGATTT | AGTGCTTTAC | GGCACCTCGA |
| CCCCAAAAAA | CTTGATTAGG | GTGATGGTTC | ACGTAGTGGG | CCATCGCCCT | GATAGACGGT | TTTTCGCCCT | TTGACGTTGG | AGTCCACGTT |
| CTTTAATAGT | GGACTCTTGT | TCCAAACTGG | AACAACACTC | AACCCTATCT | CGGTCTATTC | TTTGATTTTA | TAAGGGATTT | TGCCGATTTC |
| GGCCTATTGG | TTAAAAAATG | AGCTGATTTA | ACAAAAATTT | AACGCGAATT | TTAACAAAAT | ATTAACGCTT | ACAATTTCCA | TTCGCCATTC |
| AGGCTGCGCA | ACTGTTGGGA | AGGGCGATCG | GTGCGGGCCT | CTTCGCTATT | ACGCCAGCTG | GCGAAAGGGG | GATGTGCTGC | AAGGCGATTA |
| AGTTGGGTAA | CGCCAGGGTT | TTCCCAGTCA | CGACGTTGTA | AAACGACGGC | CAGTGAGCGC | GCGTAATACG | ACTCACTATA | GGGCGAATTG |
| GAGCTCCACC | GCGGTGGCGG | CCGCTCTAGA | ACTAGTGGAT | CCCCCGGGCT | GCAGGAATTC | GATATCAAGC | TTATCGATAC | CGTCGACCTC |
| GAGGGGGGGC | CCGGTACCCA | GCTTTTGTTC | CCTTTAGTGA | GGGTTAATTT | CGAGCTTGGC | GTAATCATGG | TCATAGCTGT | TTCCTGTGTG |
| AAATTGTTAT | CCGCTCACAA | TTCCACACAA | CATACGAGCC | GGAAGCATAA | AGTGTAAAGC | CTGGGGTGCC | TAATGAGTGA | GCTAACTCAC |
| ATTAATTGCG | TTGCGCTCAC | TGCCCGCTTT | CCAGTCGGGA | AACCTGTCGT | GCCAGCTGCA | TTAATGAATC | GGCCAACGCG | CGGGGAGAGG |
| CGGTTTGCGT | ATTGGGCGCT | CTTCCGCTTC | CTCGCTCACT | GACTCGCTGC | GCTCGGTCGT | TCGGCTGCGG | CGAGCGGTAT | CAGCTCACTC |
| AAAGGCGGTA | ATACGGTTAT | CCACAGAATC | AGGGGATAAC | GCAGGAAAGA | ACATGTGAGC | AAAAGGCCAG | CAAAAGGCCA | GGAACCGTAA |
| AAAGGCCGCG | TTGCTGGCGT | TTTTCCATAG | GCTCCGCCCC | CCTGACGAGC | ATCACAAAAA | TCGACGCTCA | AGTCAGAGGT | GGCGAAACCC |
| GACAGGACTA | TAAAGATACC | AGGCGTTTCC | CCCTGGAAGC | TCCCTCGTGC | GCTCTCCTGT | TCCGACCCTG | CCGCTTACCG | GATACCTGTC |
| CGCCTTTCTC | CCTTCGGGAA | GCGTGGCGCT | TTCTCATAGC | TCACGCTGTA | GGTATCTCAG | TTCGGTGTAG | GTCGTTCGCT | CCAAGCTGGG |
| CTGTGTGCAC | GAACCCCCCG | TTCAGCCCGA | CCGCTGCGCC | TTATCCGGTA | ACTATCGTCT | TGAGTCCAAC | CCGGTAAGAC | ACGACTTATC |
| GCCACTGGCA | GCAGCCACTG | GTAACAGGAT | TAGCAGAGCG | AGGTATGTAG | GCGGTGCTAC | AGAGTTCTTG | AAGTGGTGGC | CTAACTACGG |
| CTACACTAGA | AGAACAGTAT | TTGGTATCTG | CGCTCTGCTG | AAGCCAGTTA | CCTTCGGAAA | AAGAGTTGGT | AGCTCTTGAT | CCGGCAAACA |
| AACCACCGCT | GGTAGCGGTG | GTTTTTTTGT | TTGCAAGCAG | CAGATTACGC | GCAGAAAAAA | AGGATCTCAA | GAAGATCCTT | TGATCTTTTC |
| TACGGGGTCT | GACGCTCAGT | GGAACGAAAA | CTCACGTTAA | GGGATTTTGG | TCATGAGATT | ATCAAAAAGG | ATCTTCACCT | AGATCCTTTT |
| AAATTAAAAA | TGAAGTTTTA | AATCAATCTA | AAGTATATAT | GAGTAAACTT | GGTCTGACAG | TTACCAATGC | TTAATCAGTG | AGGCACCTAT |
| CTCAGCGATC | TGTCTATTTC | GTTCATCCAT | AGTTGCCTGA | CTCCCCGTCG | TGTAGATAAC | TACGATACGG | GAGGGCTTAC | CATCTGGCCC |
| CAGTGCTGCA | ATGATACCGC | GAGACCCACG | CTCACCGGCT | CCAGATTTAT | CAGCAATAAA | CCAGCCAGCC | GGAAGGGCCG | AGCGCAGAAG |
| TGGTCCTGCA | ACTTTATCCG | CCTCCATCCA | GTCTATTAAT | TGTTGCCGGG | AAGCTAGAGT | AAGTAGTTCG | CCAGTTAATA | GTTTGCGCAA |
| CGTTGTTGCC | ATTGCTACAG | GCATCGTGGT | GTCACGCTCG | TCGTTTGGTA | TGGCTTCATT | CAGCTCCGGT | TCCCAACGAT | CAAGGCGAGT |
| TACATGATCC | CCCATGTTGT | GCAAAAAAGC | GGTTAGCTCC | TTCGGTCCTC | CGATCGTTGT | CAGAAGTAAG | TTGGCCGCAG | TGTTATCACT |
| CATGGTTATG | GCAGCACTGC | ATAATTCTCT | TACTGTCATG | CCATCCGTAA | GATGCTTTTC | TGTGACTGGT | GAGTACTCAA | CCAAGTCATT |
| CTGAGAATAG | TGTATGCGGC | GACCGAGTTG | CTCTTGCCCG | GCGTCAATAC | GGGATAATAC | CGCGCCACAT | AGCAGAACTT | TAAAAGTGCT |
| CATCATTGGA | AAACGTTCTT | CGGGGCGAAA | ACTCTCAAGG | ATCTTACCGC | TGTTGAGATC | CAGTTCGATG | TAACCCACTC | GTGCACCCAA |
| CTGATCTTCA | GCATCTTTTA | CTTTCACCAG | CGTTTCTGGG | TGAGCAAAAA | CAGGAAGGCA | AAATGCCGCA | AAAAAGGGAA | TAAGGGCGAC |
| ACGGAAATGT | TGAATACTCA | TACTCTTCCT | TTTTCAATAT | TATTGAAGCA | TTTATCAGGG | TTATTGTCTC | ATGAGCGGAT | ACATATTTGA |
| ATGTATTTAG | AAAAATAAAC | AAATAGGGGT | TCCGCGCACA | TTTCCCCGAA | AAGTGCCACC | TGACGTCTAA | GAAACCATTA | TTATCATGAC |
| ATTAACCTAT | AAAAATAGGC | GTATCACGAG | GCCCTTTCGT | C | | | | |

```
CGCCAGGCTC AAGGCGCGCA TGCCCCGACGG CGAGGATCTC GTCGTGACCC ATGGCGATGC CTGCTTGCCG AATATCATGG TGGAAAAATGG CCGCTTTTCT
GGATTCATCG ACTGTGGCCG GCTGGGTGTG GCGGACCGCT ATOAGGACAT AGCGTTGGCT ACCCGTGATA TTGCTGAAGA GCTTGGCGGC GAATGGGCTG
ACCGCTTCCT CGTGCTTTAC GGTATCGCCG CTCCCGATTC GCAGCGCATC GCCTTCTATC GCAGTTCTTC TGAGCGGGAC TCTGGGGTTC
GAAATGACCG ACCAAGCGAC GCCCAACCTG CCATCACGAG ATTTCGATTC CACCGCCGCG TTCTATGAAA GGTTGGGCTT CGGAATCGTT TTCCGGGACG
CCGGCTGGAT GATCCTCCAG CGCGGGGATC TCATGCTGGA GTTCTTCGCC CACCCCAACT TGTTTATTGC AGCTTATAAT GGTTACAAAT AAAGCAATAG

-continued
CATCACAAAT TTCACAAATA AGCATTTTT TTCACTGCAT TCTAGTTGTG GTTTGTCCAA ACTCATCAAT GTATCTTATC ATGTCTGACC
TCTAGCTAGA GCTTGGCGTA ATCATGGTCA TAGCTGTTTC CTGTGTGAAA TTGTTATCCG CTCACAATTC CACACAACAT ACGAGCCGGA AGCATAAAGT
GTAAAGCCTG GGGTGCCTAA TGAGTGAGCT AACTCACATT AATTGCGTTG CGCTCACTGC CCGCTTTCCA GTCGGGAAAC CTGTCGTGCC AGCTGCATTA
ATGAATGGCC CAACGCGCGG GGAGAGGCGG TTTGCGTATT GGGCGCTCTT CGCTCACTGAC GCTGCGCTCG GTCGTTCG CGGAATCGGG GCTGCGGCGA
GCGGTATCAG CTCACTCAAA GGCGGTAATA CGGTTATCCA CAGAATCAGG GGATAACGCA GGAAAGAACA TGTGAGCAAA AGGCCAGCAA AAGGCCAGGA
ACCGTAAAAA GGCCGCGTTG CTGGCGTTTT TCCATAGGCT CCGCCCCCCT GACGAGCATC ACAAAAATCG ACGCTCAAGT CAGAGGTGGC GAAACCCGAC
AGGACTATAA AGATACCAGG CGTTTCCCCC TGGAAGCTCC CTCGTGTTCC GACCCTGCCG CTTACCGGAT ACCTGTCCGC CTTTCTCCCT
TCGGAAGCG TGGCGCTTTC TCATAGCTCA CGCTGTAGGT ATCTCAGTTC GGTGTAGGTC GTTCGCTCCA AGCTGGGCTG TGTGCACGAA CCCCCCGTTC
AGCCCGACCG CTGCGCCTTA TCCGGTAACT ATCGTCTTGA GTCCAACCCG GTAAGACACG ACTTATCGCC ACTGGCAGTA GCCACTGGTA ACAGGATTAG
CAGAGCGAGG TATGTAGGCG GTGCTACAGA GTTCTTGAAG TGGTGGCCTA ACTACGGCTA CACTAGAAGA ACAGTATTTG GTATCTGCGC TCTGCTGAAG
CCAGTTACCT TCGGAAAAAG AGTTGGTAGC TCTTGATCCG GCAAACAAAC CACCGCTGGT AGCGGTTTTT TTGTTTGCAA GCAGCAGATT ACGCGCAGAA
AAAACGATC AAAGGATCTT CCTTTGATCT TTTCTACGGG GTCTGACGCT CAGTGGAACG AAAACTCACG TTAAGGGATT TTGGTCATGA GATTATCAAA
AAGGATCTTC ACCTAGATCC TTTTAAATTA AAAATGAAGT TTTAAATCAA TCTAAAGTAT ATATGAGTAA ACTTGGTCTG ACAGTTACCA ATGCTTAATC
AGTGAGGCAC CTATCTCAGC GATCTGTCTA TTTCGTTCAT CCATATCCA CTGACTCCCC GTCGTGTAGA TAACTACGAT ACGGGAGGGC TTACCATCTG
GCCCCAGTGC TGCAATGATA CCGCGAGACC CACGCTCACC GGCTCCAGAT TTATCAGCAA TAAACCAGCC AGCCGGAAGG GCCGAGCGCA GAAGTGGTCC
TGCACTTTA TCCGCCTCCA TCCAGTCTAT TAATTGTTGC CGGGAAGCTA GAGTAAGTAG TTCGCCAGTT AATAGTTTGC TGCCATTGCT
ACAGGCATCG TGGTGTCACG CTCGTCGTTT GGTATGGCTT CATTCAGCTC CGGTTCCCAA CGATCAAGGC GAGTTACATG ATCCCCCATG TTGTGCAAAA
AAGCGGTTAG CTCCTTCGGT CCTCCGATCG TTGTCAGAAG TAAGTTGGCC GCAGTGTTAT CACTCATGGT TATGGCAGCA CACTTACTGT CTCTTACTGT
CATGCCATCC GTAAGATGCT TTTCTGTGAC TGGTGAGTAC TCAACCAAGT CATTCTGAGA ATAGTGTATG CGGCGACCGA GTTGCTCTTG CCCGGCGTCA
ATACGGGATA ATACCGCGCC ACATAGCAGA ACTTTAAAAG TGCTCATCAT TGGAAAACGT TCTTCGGGGC GAAAACTCTC AAGGATCTTA CCGCTGTTGA
GATCCAGTTC GATGTAACCC ACTCGTGCAC CCAACTGATC TTCAGCATCT TTTACTTTCA CCAGCGTTTC TGGGTGAGCA AAAACAGGAA GGCAAAATGC
CGCAAAAAAG GGAATAAGGG CGACACGGAA CGACACGGAA GGAATAAGGG ATGTTATTGA AGCATTTATC AGGGTTATTG TCTCATGAGC
GGATACATAT TTGAATGTAT TTAGAAAAAT AAACAAATAG GGGTTCCGCG CACATTTCCC CGAAAAGTGC CACCTGACGT C
``` pVAX1HGF/MGB1

SEQ ID NO. 3

GCTGCTTCGCGATGTACGGGCCAGATATACGCGTTGACATTGATTATTGA
CTAGTTATTAATAGTAATCAATTACGGGGTCATTAGTTCATAGCCCATAT
ATGGAGTTCCGCGTTACATAACTTACGGTAAATGGCCCGCCTGGCTGACC
GCCCAACGACCCCCGCCCATTGACGTCAATAATGACGTATGTTCCCATAG
TAACGCCAATAGGGACTTTCCATTGACGTCAATGGGTGGAGTATTTACGG
TAAACTGCCCACTTGGCAGTACATCAAGTGTATCATATGCCAAGTACGCC
CCCTATTGACGTCAATGACGGTAAATGGCCCGCCTGGCATTATGCCCAGT
ACATGACCTTATGGGACTTTCCTACTTGGCAGTACATCTACGTATTAGTC
ATCGCTATTACCATGGTGATGCGGTTTTGGCAGTACATCAATGGGCGTGG
ATAGCGGTTTGACTCACGGGGATTTCCAAGTCTCCACCCCATTGACGTCA
ATGGGAGTTTGTTTTGGCACCAAAATCAACGGGACTTTCCAAAATGTCGT
AACAACTCCGCCCCATTGACGCAAATGGGCGGTAGGCGTGTACGGTGGGA
GGTCTATATAAGCAGAGCTCTCTGGCTAACTAGAGAACCCACTGCTTACT
GGCTTATCGAAATTAATACGACTCACTATAGGGAGACCCAAGCTGGCTAG
CGTTTAAACTTAAGCTTGGTACCGAGCTCGGATCCGCCAGCCCGTCCAGC
AGCACCATGTGGGTGACCAAACTCCTGCCAGCCCTGCTGCTGCAGCATGT
CCTCCTGCATCTCCTCCTGCTCCCCATCGCCATCCCCTATGCAGAGGGAC
AAAGGAAAGAAGAAATACAATTCATGAATTCAAAAAATCAGCAAAGACT
ACCCTAATCAAAATAGATCCAGCACTGAAGATAAAAACCAAAAAGTGAA
TACTGCAGACCAATGTGCTAATAGATGTACTAGGAATAAAGGACTTCCAT
TCACTTGCAAGGCTTTTGTTTTTGATAAAGCAAGAAAACAATGCCTCTGG
TTCCCCTTCAATAGCATGTCAAGTGGAGTGAAAAAAGAATTTGGCCATGA
ATTTGACCTCTATGAAAACAAAGACTACATTAGAAACTGCATCATTGGTA
AAGGACGCAGCTACAAGGGAACAGTATCTATCACTAAGAGTGGCATCAAA
TGTCAGCCCTGGAGTTCCATGATACCACACGAACACAGCTTTTTGCCTTC
GAGCTATCGGGGTAAAGACCTACAGGAAAACTACTGTCGAAATCCTCGAG
GGGAAGAAGGGGGACCCTGGTGTTTCACAAGCAATCCAGAGGTACGCTAC
GAAGTCTGTGACATTCCTCAGTGTTCAGAAGTTGAATGCATGACCTGCAA
TGGGGAGAGTTATCGAGGTCTCATGGATCATACAGAATCAGGCAAGATTT
GTCAGCGCTGGGATCATCAGACACCACACCGGCACAAATTCTTGCCTGAA
AGATATCCCGACAAGGGCTTTGATGATAATTATTGCCGCAATCCCGATGG
CCAGCCGAGGCCATGGTGCTATACTCTTGACCCTCACACCCGCTGGGAGT
ACTGTGCAATTAAAACATGCGCTGACAATACTATGAATGACACTGATGTT
CCTTTGGAAACAACTGAATGCATCCAAGGTCAAGGAGAAGGCTACAGGGG
CACTGTCAATACCATTTGGAATGGAATTCCATGTCAGCGTTGGGATTCTC
AGTATCCTCACGAGCATGACATGACTCCTGAAAATTTCAAGTGCAAGGAC
CTACGAGAAAATTACTGCCGAAATCCAGATGGGTCTGAATCACCCTGGTG
TTTTACCACTGATCCAAACATCCGAGTTGGCTACTGCTCCCAAATTCCAA
ACTGTGATATGTCACATGGACAAGATTGTTATCGTGGGAATGGCAAAAAT

-continued

TATATGGGCAACTTATCCCAAACAAGATCTGGACTAACATGTTCAATGTG
GGACAAGAACATGGAAGACTTACATCGTCATATCTTCTGGGAACCAGATG
CAAGTAAGCTGAATGAGAATTACTGCCGAAATCCAGATGATGATGCTCAT
GGACCCTGGTGCTACACGGGAAATCCACTCATTCCTTGGGATTATTGCCC
TATTTCTCGTTGTGAAGGTGATACCACACCTACAATAGTCAATTTAGACC
ATCCCGTAATATCTTGTGCCAAAACGAAACAATTGCGAGTTGTAAATGGG
ATTCCAACACGAACAAACATAGGATGGATGGTTAGTTTGAGATACAGAAA
TAAACATATCTGCGGAGGATCATTGATAAAGGAGAGTTGGGTTCTTACTG
CACGACAGTGTTTCCCTTCTCGAGACTTGAAAGATTATGAAGCTTGGCTT
GGAATTCATGATGTCCACGGAAGAGGAGATGAGAAATGCAAACAGGTTCT
CAATGTTTCCCAGCTGGTATATGGCCCTGAAGGATCAGATCTGGTTTTAA
TGAAGCTTGCCAGGCCTGCTGTCCTGGATGATTTTGTTAGTACGATTGAT
TTACCTAATTATGGATGCACAATTCCTGAAAAGACCAGTTGCAGTGTTTA
TGGCTGGGGCTACACTGGATTGATCAACTATGATGGCCTATTACGAGTGG
CACATCTCTATATAATGGGAAATGAGAAATGCAGCCAGCATCATCGAGGG
AAGGTGACTCTGAATGAGTCTGAAATATGTGCTGGGGCTGAAAAGATTGG
ATCAGGACCATGTGAGGGGGATTATGGTGGCCCACTTGTTTGTGAGCAAC
ATAAAATGAGAATGGTTCTTGGTGTCATTGTTCCTGGTCGTGGATGTGCC
ATTCCAAATCGTCCTGGTATTTTTGTCCGAGTAGCATATTATGCAAAATG
GATACACAAAATTATTTTAACATATAAGGTACCACAGTCATAGCTGTTAA
CCCGGGTCGAAGCGGCCGCTCGAGTCTAGAGGGCCCGTTTAAACCCGCTG
ATCAGCCTCGACTGTGCCTTCTAGTTGCCAGCCATCTGTTGTTTGCCCCT
CCCCCGTGCCTTCCTTGACCCTGGAAGGTGCCACTCCCACTGTCCTTTCC
TAATAAAATGAGGAAATTGCATCGCATTGTCTGAGTAGGTGTCATTCTAT
TCTGGGGGGTGGGGTGGGCAGGACAGCAAGGGGGAGGATTGGGAAGACA
ATAGCAGGCATGCTGGGGATGCGGTGGGCTCTATGGCTTCTACTGGGCGG
TTTTATGGACAGCAAGCGAACCGGAATTGCCAGCTGGGGCGCCCTCTGGT
AAGGTTGGGAAGCCCTGCAAAGTAAACTGGATGGCTTTCTTGCCGCCAAG
GATCTGATGGCGCAGGGGATCAAGCTCTGATCAAGAGACAGGATGAGGAT
CGTTTCGCATGATTGAACAAGATGGATTGCACGCAGGTTCTCCGGCCGCT
TGGGTGGAGAGGCTATTCGGCTATGACTGGGCACAACAGACAATCGGCTG
CTCTGATGCCGCCGTGTTCCGGCTGTCAGCGCAGGGGCGCCCGGTTCTTT
TTGTCAAGACCGACCTGTCCGGTGCCCTGAATGAACTGCAAGACGAGGCA
GCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGC
CGGGGCAGGATCTCCTGTCATCTCACCTTGCTCCTGCCGAGAAAGTATCC
ATCATGGCTGATGCAATGCGGCGGCTGCATACGCTTGATCCGGCTACCTG
CCCATTCGACCACCAAGCGAAACATCGCATCGAGCGAGCACGTACTCGGA
TGGAAGCCGGTCTTGTCGATCAGGATGATCTGGACGAAGAGCATCAGGGG
CTCGCGCCAGCCGAACTGTTCGCCAGGCTCAAGGCGAGCATGCCCGACGG

-continued
CGAGGATCTCGTCGTGACCCATGGCGATGCCTGCTTGCCGAATATCATGG
TGGAAAATGGCCGCTTTTCTGGATTCATCGACTGTGGCCGGCTGGGTGTG
GCGGACCGCTATCAGGACATAGCGTTGGCTACCCGTGATATTGCTGAAGA
GCTTGGCGGCGAATGGGCTGACCGCTTCCTCGTGCTTTACGGTATCGCCG
CTCCCGATTCGCAGCGCATCGCCTTCTATCGCCTTCTTGACGAGTTCTTC
TGAATTATTAACGCTTACAATTTCCTGATGCGGTATTTTCTCCTTACGCA
TCTGTGCGGTATTTCACACCGCATCAGGTGGCACTTTTCGGGGAAATGTG
CGCGGAACCCCTATTTGTTTATTTTTCTAAATACATTCAAATATGTATCC
GCTCATGAGACAATAACCCTGATAAATGCTTCAATAATAGCACGTGCTAA
AACTTCATTTTTAATTTAAAAGGATCTAGGTGAAGATCCTTTTTGATAAT
CTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGT -continued
TTGCCGGATCAAGAGCTACCAACTCTTTTTCCGAAGGTAACTGGCTTCAG
CAGAGCGCAGATACCAAATACTGTTCTTCTAGTGTAGCCGTAGTTAGGCC
ACCACTTCAAGAACTCTGTAGCACCGCCTACATACCTCGCTCTGCTAATC
CTGTTACCAGTGGCTGCTGCCAGTGGCGATAAGTCGTGTCTTACCGGGTT
GGACTCAAGACGATAGTTACCGGATAAGGCGCAGCGGTCGGGCTGAACGG
GGGGTTCGTGCACACAGCCCAGCTTGGAGCGAACGACCTACACCGAACTG
AGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCA
CGAGGGAGCTTCCAGGGGAAACGCCTGGTATCTTTATAGTCCTGTCGGG
TTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGG
CCTTTTGCTGGCCTTTTGCTCACATGTTCTT

---

What is claimed:

1. A method for decreasing necrosis of a flap or skin graft in a subject undergoing flap or skin graft surgery, comprising administering to the subject prior to the surgery, by injection at or near the planned site of flap or skin graft, a vector that comprises a nucleic acid sequence encoding human hepatocyte growth factor, wherein said vector is a plasmid selected from the group consisting of pcDNA3.1(−) and pVAX1 and comprises the nucleic acid sequence of SEQ ID NO:1 and the CMV promoter, wherein the area of necrosis in the flap or skin graft is decreased as compared to a subject who has not been injected with said vector.

2. The method of claim 1, wherein said flap is selected from the group consisting of a skin flap, a muscle flap, a myocutaneous flap and a cartilocutaneous flap.

3. The method of claim 1, wherein said vector is administered at least 3-14 days prior to flap or skin graft surgery.

4. The method of claim 1, wherein said vector is administered at least 5-10 days prior to flap or skin graft surgery.

5. The method of claim 1, wherein said vector is administered at least 7 days prior to flap or skin graft surgery.

6. The method of claim 1, wherein said vector is administered intramuscularly.

7. The method of claim 6, wherein said vector is administered in the rectus abdominus muscle.

8. The method of claim 1, wherein said vector is pVAX1.

9. The method of claim 8, wherein said vector comprises the sequence of SEQ ID NO. 2.

10. The method of claim 8, wherein said vector comprises sequence of SEQ ID NO. 3.

11. The method of claim 1, wherein the subject is a human.

12. The method of claim 1, wherein said vector is pcDNA3.1(−).

* * * * *